US008501424B2

(12) United States Patent
Harding

(10) Patent No.: US 8,501,424 B2
(45) Date of Patent: Aug. 6, 2013

(54) CD4+ EPITOPES OF BONE MORPHOGENETIC PROTEINS

(75) Inventor: Fiona A. Harding, Santa Clara, CA (US)

(73) Assignee: Danisco US Inc., Palo Alto, CA (US)

( * ) Notice: Subject to any disclaimer, the term of this patent is extended or adjusted under 35 U.S.C. 154(b) by 1303 days.

(21) Appl. No.: 10/574,314

(22) PCT Filed: Oct. 21, 2004

(86) PCT No.: PCT/US2004/034679
§ 371 (c)(1),
(2), (4) Date: Jun. 22, 2007

(87) PCT Pub. No.: WO2005/044838
PCT Pub. Date: May 19, 2005

(65) Prior Publication Data

US 2007/0275417 A1 Nov. 29, 2007

Related U.S. Application Data

(60) Provisional application No. 60/517,035, filed on Nov. 3, 2003.

(51) Int. Cl.
*G01N 33/00* (2006.01)
*C12P 19/34* (2006.01)
*C07H 21/04* (2006.01)

(52) U.S. Cl.
USPC ......................... 435/7.24; 435/91.1; 435/91.2

(58) Field of Classification Search
None
See application file for complete search history.

(56) References Cited

U.S. PATENT DOCUMENTS

2003/0185792 A1 10/2003 Keck et al.

FOREIGN PATENT DOCUMENTS

WO WO 99/26975 6/1999
WO WO 02/077187 A2 * 10/2002
WO WO 03/042656 5/2003

OTHER PUBLICATIONS

Walker and Wright. (Neurosurg. Focus 13(6): 1-13, 2002).*
Paul (Fundamental Immunology 4th Edition, 1999, p. 12, Lippincott-Raven Publishers, Philadelphia/New York).*
Altschul, S. et al., "Multiple Alignment and Phytogenetic Trees" Meth. Enzymol.,, 266:460-480 [1996].
Altschul, S. et al., "Basic Local Alignment Search Tool" J. Mol. Biol. 215:403-410 [1990].
Feng, D-F. et al. "Progressive Sequence Alignment as a Prerequisite to Correct Phylogenic Trees", J. Mol. Evol., 25:351-360 [1987].
Gould, S. et al. "BMP-7 regulates chemokine, cytokine, and hemodynamic gene expression in proximal tubule cells", Kidney Int'l, 61:51 [2002].
Grusby, M. et al. "Mice Lacking Major Histocompatibility Complex Class I and Class II Molecules"Proc. Natl. Acad. Sci., 90:3913-3917 [1993].
Henikoff, S. and Henikoff, JG, "Amino Acid Substitution Matrices from Protein Blocks" Proc. Natl. Acad. Sci. USA 89:10915-10919 [1989].
Herman, A. et al. "Determination of Glutamic Acid Decaroxylase 65 Peptides Presented by the Type I Diabetes-Associated HLA-DQ8 Class II Molecule Identifies an Immunogenic Peptide Motif", J. Immunol., 163:6275-6282 [1999].
Higgins, D. et al. "Fast and Sensitive Multiple Sequence Alignments on a Microcomputer" CABIOS Comm. 5:151-153 [1989].
Higgins, D. et al. "CLUSTAL: A Package for Performing Multiple Sequence Alignment on a Microcomputer", Gene 73:237-244 [1988].
Karlin, S. et al. "Applications and Statistics for Multiple High-Scoring Segments in Molecular Sequences", Proc. Natl. Acad. Sci. USA 90:5873-5787 [1993].
Pearson, W. et al. "Improved Tools for Biological Sequence Comparison" Proc. Natl. Acad. Sci. USA 85:2444-2448 [1988].
Sambrook, J et al., Molecular Cloning: A Laboratory Manual, 2nd ed., Cold Spring Harbor Laboratory Press, New York [1989], pp. 16.7-16.8.
Sonderstrup, G. et al., "HLA Class II Transgenic Mice: Models of the Human CD4 T-Cell Immune Response", Immunol, Rev., 172: 335-343 [1999].
Taneja, V. et a. "HLA Class II Transgenic Mice as Models of Human Diseases", Immunol. Rev., 169:67-79 [1999].
Zeisberg, M. et al. "BMP-7 Counteracts TGF-β1-Induced Epithelial-to-Mesenchymal Transisition and Reverses Chronic Renal Injury", Nat. Med., 9:964-968 [2003].
Chang, et al., "Cartilage-derived morphogenetic proteins. New members of the transforming growth factor-beta superfamily predominantly expressed in long bones during human embryonic development", J Biol Chem, 269:28227-34 [1994].
Database UniProt [Online] Nov. 1, 1990, "RecName: Full=Bone morphogenetic protein 7; Short=BMP-7; AltName: Full=Osteogenic protein 1; Short=OP-1; AltName: INN=Eptotermin alfa; Flags: Precursor;" XP002495782 retrieved from EBI accession No. UNIPROT:P18075 Database accession No. P18075.
Database UniProt [Online] Nov. 1, 1995, "RecName: Full=Growth/differentiation factor 5; Short=GDF-5; AltName: Full=Cartilagederived morphogenetic protein 1; Short=CDMP-1; AltName: Full=Radotermin; Flags: Precursor;" XP002495783 retrieved from EBI accession No. UNIPROT:P43026 Database accession No. P43026.
Ozkaynak, et al., "OP-1 cDNA encodes an osteogenic protein in the TGF-beta family", EMBO J, 9:2085-93 [1990].
Pilitsis et al.: 'Bone healing and spinal fusion' NEUROSURG.FOCUS vol. 13, No. 6, 2002, pp. 1-13, XP002987908.
Stickler, et al., "A human dendritic cell-based method to identify CD4+ T-cell epitopes in potential protein allergens", Environ Health Perspect, 111:251-4 [2003].

* cited by examiner

*Primary Examiner* — G. R. Ewoldt
*Assistant Examiner* — Marianne Dibrino
(74) *Attorney, Agent, or Firm* — Danisco US Inc.

(57) ABSTRACT

The present invention provides CD4+ T-cell epitopes in bone morphogenetic proteins (BMPs). In particular embodiments, the present invention provides CD4+ T-cell epitopes of BMP-7 and BMP-14. In some preferred embodiments, the present invention provides CD4+ T-cell epitopes of BMP-7 and BMP-14 that are suitable for modification to reduce the immunogenicity of the BMP-7 and BMP-14 proteins.

5 Claims, 4 Drawing Sheets

Panel A

Panel B

Panel A

Panel B

Panel A

Panel B

Panel A

Panel B

CD4+ EPITOPES OF BONE MORPHOGENETIC PROTEINS

CROSS REFERENCE TO RELATED APPLICATIONS

This application is a 371 National Phase Patent Application of PCT/US04/34679, filed on Oct. 21, 2004, which claims the benefit of US. Provisional Patent Application No. 60/517,035, filed on Nov. 3, 2003, the disclosure of which is incorporated herein in its entirety.

FIELD OF THE INVENTION

The present invention provides CD4+ T-cell epitopes in bone morphogenetic proteins (BMPs). In particular embodiments, the present invention provides CD4+ T-cell epitopes of BMP-7 and BMP-14. In some preferred embodiments, the present invention provides CD4+ T-cell epitopes of BMP-7 and BMP-14 that are suitable for modification to reduce the immunogenicity of BMP-7 and BMP-14 proteins.

BACKGROUND OF THE INVENTION

"Bone morphogenetic protein" ("BMP") is the generic term used to refer to a family of proteins originally identified in demineralized bone extracts. These proteins, found in minute amounts in bone material (approximately 1 μg/kg dry weight of bone) were found to be capable of inducing bone formation at ectopic sites. While the term "BMP" is indicative of their properties, these proteins also have other functions and are involved in processes other than bone formation.

The BMP Family of Proteins

With the exception of BMP-1, the BMP proteins are within the transforming growth factor beta ("TGF-β") superfamily of proteins. Among the different morphogenetic proteins there is a considerable species conservation, with several species having proteins that are identical. The BMP family comprises a series of proteins, including those described below. BMP-1 (730 amino acids, including 22 amino acids encoding a signal sequence) is a cysteine-rich zinc-peptidase that cleaves several pro-collagens into fragments that form mature collagen fibrils. It is identical with procollagen C-proteinase, a metalloproteinase involved in extracellular matrix (ECM) formation. BMP-2A (also known as "BMP-2α," and "BMP-2 alpha") has been renamed BMP-2. The 114 amino acids of this factor have been shown to be identical in human, mouse and rat proteins. In addition, the protein shows 68% homology with *Drosophila* dpp (i.e., "decapentaplegic," a locus involved in embryonic development). BMP-2B (BMP-2β) is a factor comprising 116 amino acids, that has been renamed "BMP-4." The mouse and rat BMP-4 proteins are identical in their amino acid sequences. BMP-3 (110 amino acids) is a glycoprotein that is identical to "osteogenin." The mature human and rat BMP-3 proteins are 98% identical. There is also a closely related factor in *Xenopus laevis*. BMP-3β (110 amino acids) is related to BMP-3, sharing 82% identity. Human and mouse proteins show 97% identity (3 different amino acids), while human and rat protein sequences only differ by two amino acids. Furthermore, the factor is identical to GDF-10 (i.e., "growth/differentiation factor-10"). As indicated above, BMP4 is identical to BMP-2β. In addition, it is identical with DVR-4 (i.e., "decapentaplegic-Vg-related-4"). Also, the protein shows 72% homology with *Drosophila* dpp. In addition, BMP4 has been shown to bind to noggin and chordin. BMP-5 is a protein comprised of 138 amino acids. The human and mouse BMP-5 proteins are 96% identical. BMP-6 (139 amino acids) is identical to DVR-6 and vegetal-specific-related-1 ("Vg-1") protein. BMP-7 (139 amino acids) is identical to OP-1 ("osteogenic protein-1"). Mouse and human BMP-7 proteins are 98% identical. It is noted that the mature forms of BMP-5, BMP-6 and BMP-7 share 75% identity. BMP-8 (139 amino acids), also referred to as "BMP-8a," is identical to "OP-2." BMP-8b (139 amino acids), is identical to and sometimes referred to as "OP-3," and has only been identified in mice. BMP-9 (110 amino acids) is also referred to as "GDF-5" (i.e., "growth/differentiation factor-5"). BMP-9 may be an autocrine and paracrine mediator in the hepatic reticuloendothelial system. BMP-10 (108 amino acids) has been isolated from various sources, with the bovine and human proteins being identical. Murine BMP-10 expression has been associated with cardiac development, and it may be involved in trabeculation of the embryonic heart. BMP-11 (109 amino acids) has also been isolated from various sources, with the human and bovine sequences being identical. This protein is also referred to as "GDF-11." GMP-12 (104 amino acids) is also referred to as "GDF-7" and "CDMP-3" (i.e., "cartilage-derived morphogenetic protein-3"). BMP-13 (120 amino acids) is also known as "GDF-6" and "CDMP-2." BMP-14 (120 amino acids) is also referred to as "GDF-5" and "CDMP-1." BMP-15 (125 amino acids) has been identified in mice and humans, with the gene mapping to the X chromosome in both. The murine protein appears to be most closely related to GDF-9 and is expressed specifically in oocytes. It is also noted that some of these BMPs exist in heterodimer formation. For example, OP-1 associates with BMP-2α.

The human genes encoding BMP-1, BMP-2α and BMP-3 map to chromosomes 8, 20p12, and 4p13-21, respectively. These sequences are positioned in the vicinity of other genes involved in the formation of cartilage and bone tissues. The BMP-5 and BMP-6 genes map to human chromosome 6, while the BMP-7 gene maps to chromosome 20.

As described in greater detail below, BMPs are expressed in a variety of epithelial and mesenchymal tissues in the embryo. These proteins can be isolated from demineralized bones and osteosarcoma cells. Some BMPs (e.g., BMP-2 and BMP4) have been shown to elicit qualitatively identical effects (e.g., cartilage and bone formation) and may be able to substitute for each other.

The Function of BMP Proteins

BMPs induce the differentiation of mesenchymal-type cells into chondrocytes and osteoblasts before the initiation of bone formation. They promote the differentiation of cartilage and bone-forming cells near sites of fractures, as well as at ectopic locations. Some BMPs induce the synthesis of alkaline phosphatase and collagen in osteoblasts, while others act directly on osteoblasts and promote their maturation and suppress myogenous differentiation. Other BMPs promote the conversion of typical fibroblasts into chondrocytes and are also capable of inducing the expression of an osteoblast phenotype in non-osteogenic cell types.

Intracellular signaling following engagement of receptors for some BMP proteins has been shown to involve the action of SMAD ("Sma and Mad related") proteins. In addition, some BMPs and related factors may be involved in embryonic development. For example, osteogenin and related BMPs act as potent chemoattractants for circulating monocytes, thereby playing roles in the endochondral bone formation cascade. In addition, these factors induce the synthesis and secretion of TGF-β by monocytes, which is important in the recruitment of endothelial and mesenchymal cells and promotion of collagen and associated matrix constituent synthesis.

BMP-4 and BMP-7 are also involved in sympathetic neuron differentiation. These factors enhance the formation of adrenergic sympathetic neurons in neural crest cell cultures. This activity is also observed in vivo in developing embryos, following ectopic expression of these factors.

While some BMP activities may be enhanced by activin A and/or TGF-β, OIP ("osteogenesis inhibitory protein) antagonizes BMP activity in vivo and in vitro. Factors that were initially isolated from *Xenopus laevis* appear to act as BMP antagonists (e.g., Gremlin, Cerberus, noggin, chordin, and DAN ["differentiated screening-selected gene aberrative in neuroblastoma"]). Subsequently, similar factors were also isolated from other species.

Clinical Use and Significance of BMPs

While the clinical use of BMPs is still in its infancy, much work and interest is being dedicated to developing suitable uses for these proteins. For example, relatively impure preparations of BMPs have been used for the treatment of bone fractures. In addition, there may be a requirement for a combination of factors, including osteogenin, in order to initiate bone differentiation in bone-derived matrices. For example, osteogenin in combination with insoluble collagenous bone matrix, has been used to induce local endochondral bone differentiation in calvarial defects of adult primates. In other settings, additional components are likely to be important. For example, the osteoinductive potential of BMP preparations bound to porous β-tricalcium phosphate and the use of BMP combined with true bone ceramic as a bone grafting material have been found superior to treatment with BMPs alone for the treatment of bone tissue defects and the promotion of new bone formation.

In addition to its roles in bone formation, administration of certain members of the BMP family of proteins has also been associated with the repair and reversal of chronic renal disease. As BMP-7 has been shown to be highly expressed in the kidneys of healthy individuals, studies were conducted to determine whether the protein provides some protection against renal injury. As described by Zeisberg et al. (Zeisberg et al., Nat. Med., 9:964-968 [2003]), and Gould et al. (Gould et al., Kidney Int'l., 61:51 [2002]), administration of recombinant human BMP-7 in a mouse model of chronic renal injury resulted in the repair of severely damaged renal tubular epithelial cells and reversal of chronic renal injury. Thus, it is contemplated that BMP-7 will find use in the treatment of renal disease in humans and other animals. However, although there has been some progress in the development of compositions and methods for the use of BMPs, much remains to be done. In addition, there are questions regarding the suitability of administering these native proteins to patients.

SUMMARY OF THE INVENTION

The present invention provides CD4+ T-cell epitopes in bone morphogenetic proteins (BMPs). In particular embodiments, the present invention provides CD4+ T-cell epitopes of BMP-7 and BMP-14. In some preferred embodiments, the present invention provides CD4+ T-cell epitopes of BMP-7 and BMP-14 that are suitable for modification to reduce the immunogenicity of (e.g., native) BMP-7 and BMP-14 proteins.

The present invention provides methods for determining a T-cell epitope of a protein, wherein the protein is a BMP protein, comprising the steps of: (a) obtaining from a solution of dendritic cells and a solution of naïve CD4+ and/or CD8+ T-cells from a single human blood source; (b) differentiating the dendritic cells, in the solution of dendritic cells, to produce a solution of differentiated dendritic cells; (c) preparing a pepset of peptides from the protein; (d) combining the solution of differentiated dendritic cells and naïve CD4+ and/or CD8+ T-cells with the pepset, wherein the pepset comprises the T-cell epitope; and (e) measuring the proliferation of the T-cells in step (d).

In additional embodiments of the present invention, the methods further comprise the step of modifying the protein to produce a variant protein, wherein the variant protein exhibits an altered immunogenic response as compared to the parent (i.e., originating or source) protein. However, it is not intended that the present invention be limited to any particular combination of substitutions or other changes to the amino acid sequence of the protein.

The present invention also provides methods for reducing the immunogenicity of a BMP protein, comprising the steps of: (a) identifying at least one T-cell epitope in the protein by (i) contacting an adherent monocyte-derived dendritic cell that has been differentiated by exposure to at least one cytokine in vitro, with at least one peptide comprising the T-cell epitope; and (ii) contacting the dendritic cell and said peptide with a naïve T-cell, wherein the naïve T-cell has been obtained from the same source as the adherent monocyte-derived dendritic cell, and whereby the T-cell proliferates in response to the peptide; and (b) modifying the protein to neutralize the T-cell epitope to produce a variant protein, such that the variant protein induces less than or substantially equal to the baseline proliferation of the naïve T-cells. In some embodiments, the T-cell epitope is modified by substituting a portion of the amino acid sequence of the T-cell epitope with an analogous sequence from a homolog of the protein. In alternative embodiments, the T-cell epitope is modified by substituting the amino acid sequence of the T-cell epitope with a sequence which substantially mimics the major tertiary structure attributes of the T-cell epitope.

The present invention further provides methods for producing a variant protein having reduced allergenicity comprising the steps of: a) obtaining a naturally-occurring protein, such as a BMP protein, and preparing fragments of the naturally-occurring protein; b) contacting the fragments of the naturally-occurring protein with a first solution comprising naïve human CD4+ or CD8+ T-cells and differentiated dendritic cells; c) identifying an epitope region of the naturally-occurring protein, wherein the identifying step comprises measuring the ability of the fragments of the naturally-occurring protein epitope region to stimulate proliferation of the naïve human CD4+ or CD8+ T-cells; and d) modifying at least one amino acid in the epitope region identified in step c), to produce the variant protein. In some embodiments, the methods further comprise the step of comparing the ability of the fragments of the naturally-occurring protein to stimulate proliferation of the naïve human CD4+ or CD8+ T-cells with the ability of the fragments of the variant protein to stimulate proliferation of the naïve human CD4+ or CD8+ T-cells.

It is not intended that any of the methods of the present invention be conducted in any particular order, as far as preparation of PEPSETS™ and differentiation of dendritic cells. For example, in some embodiments the PEPSETS™ are prepared before the dendritic cells are differentiated, while in other embodiments, the dendritic cells are differentiated before the PEPSETS™ are prepared, and in still other embodiments, the dendritic cells are differentiated and the PEPSETS™ are prepared concurrently. Thus, it is not intended that the present invention be limited to methods having these steps in any particular order.

In some embodiments, the present invention provides assay systems for identification of T-cell epitopes and T-cell non-epitopes, including but not limited to methods having the steps of combining differentiated dendritic cells with human CD4+ and/or CD8+ T-cells and with a peptide of interest (e.g., peptides derived from BMPs). More specifically, peptides of interest that produce a reduced immunogenic response are provided, wherein a T-cell epitope is recognized comprising the steps of: (a) obtaining from a single blood source a solution of dendritic cells and a solution of CD4+ and/or CD8+ T-cells; (b) promoting differentiation in of the dendritic cells; (c) combining the solution of differentiated dendritic cells, CD4+ cells and/or CD8+ T-cells with a peptide of interest (e.g., a peptide comprising at least a portion of a BMP); and (d) measuring the proliferation of the T-cells in step (c).

In an embodiment of the invention, a series of peptide oligomers that correspond to all or parts of the BMP are prepared. For example, a peptide library is produced covering the relevant portion or all of BMP-7 or BMP-14. In one embodiment, the manner of producing the peptides is to introduce overlap into the peptide library, for example, producing a first peptide corresponds to amino acid sequence 1-15 of the BMP, a second peptide corresponds to amino acid sequence 4-18 of the BMP, a third peptide corresponds to amino acid sequence 7-21 of the BMP, a fourth peptide corresponds to amino acid sequence 10-24 of the BMP, etc., until representative peptides corresponding to the entire BMP molecule are created. By analyzing each of the peptides individually in the assay provided herein, it is possible to precisely identify the location of epitopes recognized by T-cells. In the example above, the greater reaction of one specific peptide than its neighbors facilitates identification of the epitope anchor region to within three amino acids. After determining the location of these epitopes, it is possible to alter the amino acids within each epitope until the peptide produces a different T-cell response from that of the original protein. Moreover, the present invention provides means for the identification of proteins that have desired low T-cell epitope potency that may be used in their naturally occurring forms.

Various in vitro and in vivo assays known in the art may be used to ascertain the reduced immunogenic response of variant proteins. In vivo assays include, but are not limited to HLA-DR3/DQ2 mouse T-cell responses, while suitable in vitro assays include, but are not limited to human peripheral blood mononuclear cell (PBMC) assays (See, Herman et al., J. Immunol., 163:6275-6282 [1999]; Sonderstrup et al., Immunol. Rev., 172: 335-343 [1999]; Taneja and David, Immunol. Rev., 169:67-79 [1999]; and Grusby et al., Proc. Natl. Acad. Sci., 90:3913-3917 [1993]).

The present invention further provides BMP compositions with reduced immunogenicity. In particular, the present invention provides such compositions that comprise epitopes described herein that reduce the immunogenic response to BMPs. In still further embodiments, the present invention provides compositions that find use in various combinations of BMPs, as well as combinations that include wild-type proteins.

In some particularly preferred embodiments, the present invention provides BMP-7 epitopes selected from the group consisting of RSQNRSKTPKNQEAL (SEQ ID NO:1), EALRMANVAENSSSD (SEQ ID NO:2), RMANVAENSSSDQRQ (SEQ ID NO:3), SFRDLGWQDWIIAPE (SEQ ID NO:4), SNVILKKYRNMVVRA (SEQ ID NO:5). In some embodiments, the present invention provides variants of these epitopes. In some preferred embodiments, the variant epitopes exhibit reduced immunogenicity, as compared to the native epitopes.

In additional particularly preferred embodiments, the present invention provides BMP-14 epitopes selected from the group consisting of SPISILFIDSANNVV (SEQ ID NO:6), PLRSHLEPTNHAVIQ (SEQ ID NO:7), and SHLEPTNHAVIQTLM (SEQ ID NO:8). In some embodiments, the present invention provides variants of these epitopes. In some preferred embodiments, the variant epitopes exhibit reduced immunogenicity, as compared to the native epitopes.

DESCRIPTION OF THE INVENTION

Figure 1:
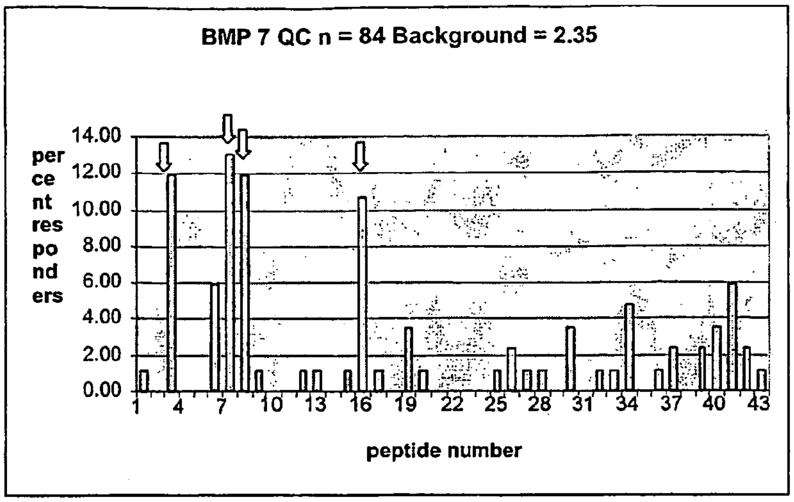
FIG. 1 provides two graphs that illustrate the percent of responders from a population of 83 random individuals tested with peptides derived from BMP-7 (Panel A) and BMP-14 (Panel B). The background and structure values are also indicated. The consecutive 15-mer peptides offset by 3 amino acids are listed on the x-axis (indicated by the "peptide number") and the percentages of donors who responded to each peptide are shown on the y-axis.
Figure 1:
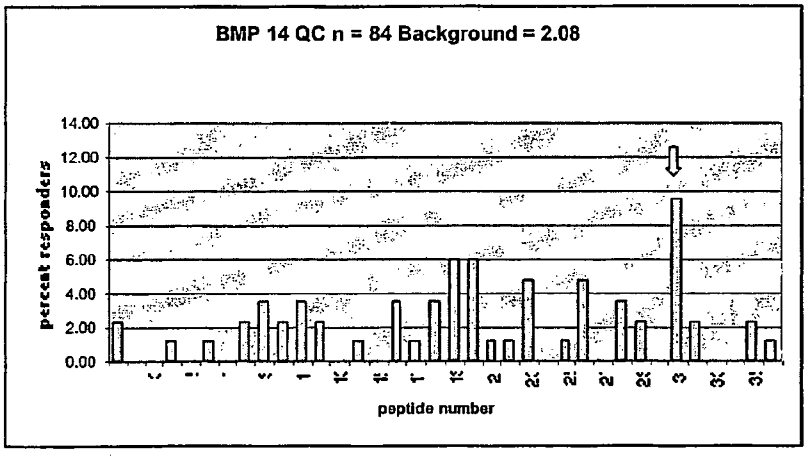

The present invention provides CD4+ T-cell epitopes in bone morphogenetic proteins (BMPs). In particular embodiments, the present invention provides CD4+ T-cell epitopes of BMP-7 and BMP-14. In some preferred embodiments, the present invention provides CD4+ T-cell epitopes of BMP-7 and BMP-14 that are suitable for modification to reduce the immunogenicity of (e.g., native) BMP-7 and BMP-14 proteins.

Definitions

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology*, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a", "an" and "the" includes the plural reference unless the context clearly indicates otherwise. To facilitate understanding of the invention, a number of terms are defined below.

As used herein, "bone morphogenetic protein" and "BMP" are used in reference to the family of proteins that are within the transforming growth factor beta ("TGF-β") superfamily of proteins (with the exception of BMP-1).

"Antigen presenting cell" as used herein refers to cells of the immune system which present antigen on their surfaces in a form that is recognizable by T-cells. Examples of antigen presenting cells are dendritic cells, interdigitating cells, activated B-cells and macrophages.

The term "lymphoid" when used in reference to a cell line or a cell, means that the cell line or cell is derived from the lymphoid lineage and includes cells of both the B and the T lymphocyte lineages.

As used herein, the terms "T lymphocyte" and "T-cell," encompass any cell within the T lymphocyte lineage from T-cell precursors (including Thy1 positive cells which have not rearranged the T-cell receptor genes) to mature T-cells (i.e., single positive for either CD4 or CD8, surface TCR positive cells).

As used herein, the terms "B lymphocyte" and "B-cell" encompasses any cell within the B-cell lineage from B-cell precursors, such as pre-B-cells ($B220^+$ cells which have begun to rearrange Ig heavy chain genes), to mature B-cells and plasma cells.

As used herein, "$CD4^+$ T-cell" and "CD4 T-cell" refer to helper T-cells (also referred to as "Th" and "$T_h$" cells), while "$CD8^+$ T-cell" and "CD8 T-cell" refer to cytotoxic T-cells (also referred to as "Tc" and "$T_c$" cells).

As used herein, "B-cell proliferation," refers to the number of B-cells produced during the incubation of B-cells with the antigen presenting cells, with or without antigen.

As used herein, "baseline B-cell proliferation," as used herein, refers to the degree of B-cell proliferation that is normally seen in an individual in response to exposure to antigen presenting cells in the absence of peptide or protein antigen. For the purposes herein, the baseline B-cell proliferation level is determined on a per sample basis for each individual as the proliferation of B-cells in the absence of antigen.

As used herein, "B-cell epitope," refers to a feature of a peptide or protein that is recognized by a B-cell receptor in the immunogenic response to the peptide comprising that antigen (i.e., the immunogen).

As used herein, "altered B-cell epitope," refers to an epitope amino acid sequence which differs from the precursor peptide or peptide of interest, such that the variant peptide of interest produces different (i.e., altered) immunogenic responses in a human or another animal. It is contemplated that an altered immunogenic response includes altered immunogenicity and/or allergenicity (i.e., an either increased or decreased overall immunogenic response). In some embodiments, the altered B-cell epitope comprises substitution and/or deletion of an amino acid selected from those residues within the identified epitope. In alternative embodiments, the altered B-cell epitope comprises an addition of one or more residues within the epitope.

As used herein "T-cell epitope" means a feature of a peptide or protein that is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II Major Histocompatibility Complex (MHC) molecules expressed on antigen-presenting cells (See e.g., Moeller (ed.), Immunol. Rev., 98:187 [1987]). In some embodiments of the present invention, the epitopes or epitopic fragments identified as described herein find use in the detection of antigen presenting cells having MHC molecules capable of binding and displaying the epitopes or fragments. In some embodiments, the epitopes/epitopic fragments further comprise a detectable label (i.e., a marker) that facilitates the identification of cells that bind and/or display the epitope/epitopic fragment of interest.

As used herein, "T-cell proliferation," refers to the number of T-cells produced during the incubation of T-cells with the antigen presenting cells, with or without antigen.

"Baseline T-cell proliferation," as used herein, refers to the degree of T-cell proliferation that is normally seen in an individual in response to exposure to antigen presenting cells in the absence of peptide or protein antigen. For the purposes herein, the baseline T-cell proliferation level is determined on a per sample basis for each individual as the proliferation of T-cells in response to antigen presenting cells in the absence of antigen.

As used herein "altered immunogenic response," refers to an increased or reduced immunogenic response. Proteins and peptides exhibit an "increased immunogenic response" when the T-cell and/or B-cell response they evoke is greater than that evoked by a parental (e.g., precursor) protein or peptide (e.g., the protein of interest). The net result of this higher response is an increased antibody response directed against the variant protein or peptide. Proteins and peptides exhibit a "reduced immunogenic response" when the T-cell and/or B-cell response they evoke is less than that evoked by a parental (e.g., precursor) protein or peptide. In some embodiments, the net result of this lower response is a reduced antibody response directed against the variant protein or peptide. In some preferred embodiments, the parental protein is a wild-type protein or peptide.

As used herein, "Stimulation Index" (SI) refers to a measure of the T-cell proliferative response of a peptide compared to a control. The SI is calculated by dividing the average CPM (counts per minute) obtained in testing the $CD4^+$ T-cell and dendritic cell culture containing a peptide by the average CPM of the control culture containing dendritic cells and $CD4^+$ T-cells but without the peptides. This value is calculated for each donor and for each peptide. While in some embodiments, SI values of between about 1.5 to 4.5 are used to indicate a positive response, the preferred SI value to indicate a positive response is between 2.5 and 3.5, inclusive; preferably between 2.7 and 3.2, inclusive; and more preferably between 2.9 and 3.1, inclusive. The most preferred embodiments described herein use a SI value of 2.95.

As used herein, the term "dataset" refers to compiled data for a set of peptides and a set of donors for tested for their responses against each test protein (i.e., a protein of interest).

As used herein, the term "pepset" refers to the set of peptides produced for each test protein (i.e., protein of interest). These peptides in the pepset (or "peptide sets") are tested with cells from each donor.

As used herein, the terms "Structure" and "Structure Value" refer to a value to rank the relative immunogenicity of proteins. The structure value is determined according to the "total variation distance to the uniform" formula below:

$$\sum\left|f(i)-\frac{1}{p}\right|$$

wherein:

Σ is the sum over all peptides in the peptide set of the absolute value of the proportion of responses to each peptide minus the frequency of that peptide in the set. f(i) is defined as the frequency of responses for an individual peptide divided by the total number of responses accumulated, and p is the number of peptides in the peptide set In preferred embodiments of the present invention, a structure value is determined for each protein tested. Based on the structure values obtained, the test proteins are ranked from the lowest value to the highest value in the series of tested proteins. In this ranked series, the lowest value indicates the least immunogenic protein, while the highest value indicates the most immunogenic protein.

In theory, if every peptide in the dataset had the same number of responses, f(i)−1/p would equal zero. In other words, the proportion of the responses at each peptide would equal the proportion of the dataset represented by one peptide, and the difference between these values would equal zero. The absolute value of the sum of the data for all the peptides (zero at each one) would equal zero. On the other hand, if all the accumulated responses were at one peptide, the value would approach 2.0. In order to insure comparability of the structure index values, a stable response pattern must be achieved within the dataset. A stable pattern is reached after enough donors have been tested to provide approximately 3 responses per peptide. Therefore, in preferred embodiments, a peptide set should be tested until there are responses across the majority of the dataset, in order for the data to accurately reflect responsivity to particular peptides and peptide regions. In most particularly preferred embodiments, there is a response to every peptide in the dataset. However, some datasets do not exhibit responses to every peptide in the dataset due to various factors (e.g., insolubility issues).

While the above formula is the preferred formula to use for determination of the structure value, other equivalent formulas find use in the present invention. For example, the "entropy of the distribution" formula finds use in the present invention, as well as various other formulae known to those in the art.

In some embodiments, the peptide sets are tested with at least as many donors as should produce 2-3 responses per peptide given the overall rate of 3% non-specific responses. Thus, in some embodiments, the number of donors is adjusted based on the number of peptides. Of course, more donors may be tested using the methods of the present invention, even when fewer peptides are present within a pepset. In some preferred embodiments, the dataset includes at least 50 donors, in order to provide good HLA allele representation.

As used herein, a "prominent response" refers to a peptide that produces an in vitro T-cell response rate in the dataset that is greater than about 2.0-fold the background response rate. In a further embodiment, the response is about a 2.0-fold to about a 5.0-fold increase above the background response rate. Also included within this term are responses that represent about a 2.5 to 3.5-fold increase, about a 2.8 to 3.2-fold increase, and a 2.9 to 3.1-fold increase above the background response rate. For example, during the development of the present invention, prominent responses were noted for some of the peptides.

As used herein, "prominent region" refers to an I-MUNE® assay response obtained with a particular peptide set that is greater than about 2.0-fold the background response rate. In one embodiment of the present invention, all of the prominent regions of a protein are reduced so that their responses in the I-MUNE® assay system of the present invention are reduced. In further embodiments, the number of prominent regions are reduced by 1, 2, 3, 4, 5, 6; 7, 8, 9, 10 or more, and preferably between 1 and 5 prominent regions are reduced in related proteins. In some embodiments, prominent regions also meet the requirements for a T-cell epitope.

As used herein, the term "major epitope" refers to an epitope (i.e., a T-cell and/or B-cell epitope), wherein the response rate within the tested donor pool is at least three standard deviations above the mean background response rate.

As used herein, the term "moderate epitope" refers to an epitope (i.e., a T-cell and/or B-cell epitope), wherein the response rate within the tested donor pool is at least two standard deviations above the mean or three times the background.

As used herein, the term "minor epitope" refers to an epitope (i.e., a T-cell and/or B-cell epitope), wherein the response rate within the tested donor pool is at least twice the background.

As used herein, the term "significant epitope" refers to an epitope (i.e., a T-cell and/or B-cell epitope), wherein the response rate within the tested donor pool is equal to or greater than about three times the background response rate.

As used herein, a "weakly significant epitope" refers to an epitope (i.e., a T-cell and/or B-cell epitope), wherein the response rate within the tested donor pool is greater than the background response rate, but less than about three times the background rate.

As used herein, "background level" and "background response" refer to the average percent of responders to any given peptide in the dataset for any tested protein. This value is determined by averaging the percent responders for all peptides in the set, as compiled for all the tested donors. As an example, a 3% background response would indicate that on average there would be three positive (SI greater than 2.95) responses for any peptide in a dataset when tested on 100 donors.

The term "sample" as used herein is used in its broadest sense. However, in preferred embodiments, the term is used in reference to a sample (e.g., an aliquot) that comprises a peptide (i.e., a peptide within a pepset, that comprises a sequence of a protein of interest) that is being analyzed, identified, modified, and/or compared with other peptides. Thus, in most cases, this term is used in reference to material that includes a protein or peptide that is of interest.

As used herein "autologous" refers to samples, sample components and other material obtained from the same source. For example, in preferred embodiments of the present invention, dendritic cells and T-cells are obtained from the same source (i.e., the same individual) and are tested together. Thus, in preferred embodiments, the cells utilized in the I-MUNE® assay system are autologous.

As used herein, the term "cytokine" refers to the soluble mediators that control many critical interactions among cells of the immune system. Cytokines comprise a diverse group of intercellular signaling peptides and glycoproteins. Most are genetically and structurally similar to each other. Each cytokine is secreted by a particular cell type in response to a variety of stimuli and produces characteristic effects on the growth, mobility, differentiation, and/or function of target cells. Collectively, cytokines regulate not only immune and inflammatory systems, but also are involved in wound healing, hematopoiesis, angiogenesis, and many other processes. It is intended that the term encompass all of the various cytokines, regardless of their structure, and commonly used nomenclature. For example, it is intended that the term encompass "lymphokines" (i.e., cytokines produced by lymphocytes), as well as "monokines" (i.e., cytokines produced by monocytes).

As used herein, "cytokine receptor" refers to receptor molecules that recognize and bind to cytokines. It is intended that the term encompass soluble cytokine receptors as well as cytokine receptors that are cell-bound. It is intended that the term also encompass modified cytokine receptor molecules (i.e., "variant cytokine receptors"), including those with substitutions, deletions, and/or additions to the cytokine receptor amino acid and/or nucleic acid sequence. Thus, it is intended that the term encompass wild-type, as well as recombinant, synthetically-produced, and variant cytokine receptors.

The term "interferon-β" ("IFN-β") as used herein, refers to one member of a large class of secretory proteins that exhibit anti-viral activity, inhibit proliferation of vertebrate cells, and modulate immune responses.

As used herein, "interleukin" ("IL") refers to a group of cytokines produced by various cells, that have numerous and varied effects on the immune system, inflammation, fever, hematopoiesis, thrombopoiesis, proliferation of lymphocytes, expression of immunoglobulins, acute phase response, activation, growth and function of various polymorphonuclear cells, etc. It is intended that the term encompass any interleukins (e.g., IL-1, IL-2, IL-3, IL-4, IL-5, etc.).

As used herein, "protein of interest," refers to a protein which is being analyzed, identified and/or modified. Naturally-occurring, as well as recombinant proteins, synthetically produced, variant and derivative proteins, all find use in the present invention.

As used herein, "protein" refers to any composition comprised of amino acids and recognized as a protein by those of skill in the art. The terms "protein," "peptide" and polypeptide are used interchangeably herein. Amino acids may be referred to by their complete names (e.g., alanine) or by the accepted one letter (e.g., A), or three letter (e.g., ala) abbreviations. Wherein a peptide is a portion of a protein, those skill in the art understand the use of the term in context. The term "protein" encompasses mature forms of proteins, as well as the pro- and prepro-forms of related proteins. Prepro forms of proteins comprise the mature form of the protein having a prosequence operably linked to the amino terminus of the protein, and a "pre-" or "signal" sequence operably linked to the amino terminus of the prosequence.

As used herein, functionally similar proteins are considered to be "related proteins." In some embodiments, these proteins are derived from a different genus and/or species, including differences between classes of organisms (e.g., a bacterial protein and a fungal protein). In additional embodiments, related proteins are provided from the same species. Indeed, it is not intended that the present invention be limited to related proteins from any particular source(s).

As used herein, the term "derivative" refers to a protein which is derived from a precursor protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

One type of related (and derivative) proteins are "variant proteins." In preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In one preferred embodiment, the number of different amino acids between variants is between 1 and 10. In particularly preferred embodiments, related proteins and particularly variant proteins comprise at least 50%, 60%, 65%. 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

In one embodiment, the prominent corresponding region of a variant produces only a background level of immunogenic response. Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence.

In some embodiments, the following cassette mutagenesis method finds use in the construction of the protein variants of the present invention, although other methods may be used. First, the naturally-occurring gene encoding the protein is obtained and sequenced in whole or in part. Then the sequence is scanned for a point at which it is desired to make a mutation (deletion, insertion or substitution) of one or more amino acids in the encoded protein. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site which is not overly redundant in the protein gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region" generally refers to an analogous position along related proteins or a parent protein.

As used herein, the term "analogous sequence" refers to a sequence within a protein that provides similar function, tertiary structure, and/or conserved residues as the protein of interest (i.e., typically the original protein of interest). In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids preferably maintain that specific structure.

As used herein, "homologous protein" refers to a protein that has similar action, structure, antigenic, and/or immunogenic response as the protein of interest. It is not intended that a homolog and a protein of interest be necessarily related evolutionarily. Thus, it is intended that the term encompass the same functional protein obtained from different species. In some preferred embodiments, it is desirable to identify a homolog that has a tertiary and/or primary structure similar to the protein of interest, as replacement for the epitope in the protein of interest with an analogous segment from the homolog will reduce the disruptiveness of the change. Thus, in most cases, closely homologous proteins provide the most desirable sources of epitope substitutions. Alternatively, it is advantageous to look to human analogs for a given protein. For example, in some embodiments, substituting a specific epitope in one human BMP type with a sequence from another BMP or other species' BMP results in the production of a BMP type that increases immunogenicity to a level suitable for use in vaccine preparations.

As used herein, "homologous genes" refers to at least a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring (i.e., precursor) protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'4, and a comparison of both strands.

As used herein, "percent (%) nucleic acid sequence identity" is defined as the percentage of nucleotide residues in a candidate sequence that are identical with the nucleotide residues of the sequence.

As used herein, the term "hybridization" refers to the process by which a strand of nucleic acid joins with a complementary strand through base pairing, as known in the art.

As used herein, "maximum stringency" refers to the level of hybridization that typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The phrases "substantially similar" and "substantially identical" in the context of two nucleic acids or polypeptides typically means that a polynucleotide or polypeptide comprises a sequence that has at least 75% sequence identity, preferably at least 80%, more preferably at least 90%, still more preferably 95%, most preferably 97%, sometimes as much as 98% and 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad Sci. USA 89:10915 [1989]; Karin et al., Proc. Natl Acad. Sci USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]).

As used herein, "equivalent residues" refers to proteins that share particular amino acid residues. For example, equivalent resides may be identified by determining homology at the level of tertiary structure for a protein (e.g. BMP) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

In some embodiments, modification is preferably made to the "precursor DNA sequence" which encodes the amino acid sequence of the precursor enzyme, but can be by the manipulation of the precursor protein. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification(s) that change the characteristics of the BMP.

In some preferred embodiments, the protein gene is ligated into an appropriate expression plasmid. The cloned protein gene is then used to transform or transfect a host cell in order to express the protein gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antimicrobial-containing media is also included.

The present invention encompasses proteins having altered immunogenicity that are equivalent. Being "equivalent," means that the proteins are encoded by a polynucleotide capable of hybridizing to the polynucleotide having the sequence as shown in any one of those provided herein, under conditions of medium to high stringency and still retaining the altered immunogenic response to human T-cells. Being "equivalent" means that the BMP comprises at least 55%, at least 65%, at least 70%, at least 75%, at least 80%, at least 85%, at least 90%, at least 95%, at least 97% or at least 99% identity to the epitope sequences and the variant BMPs having such epitopes (e.g., having the amino acid sequence modified).

As used herein, the terms "hybrid proteins" and "fusion proteins" refer to proteins that are engineered from at least two different or "parental" proteins. In preferred embodiments, these parental proteins are homologs of one another. For example, in some embodiments, a preferred hybrid BMP or fusion protein contains the N-terminus of a protein and the C-terminus of a homolog of the protein. In some preferred embodiment, the two terminal ends are combined to correspond to the full-length active protein. In alternative preferred embodiments, the homologs share substantial similarity but do not have identical T-cell epitopes. Therefore, in one embodiment, the present invention provides a BMP of interest having one or more T-cell epitopes in the C-terminus, but in which the C-terminus is replaced with the C-terminus of a homolog having a less potent T-cell epitope, or fewer or no T-cell epitopes in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

"Operably linked" and "in operable combination," when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene" means a DNA sequence comprising the coding region of a gene or, in other words, the DNA sequence that encodes a gene product. The coding region may be present in either a cDNA or genomic DNA form. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element that controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. Once transformed into a suitable host, the vector may replicate and function independently of the host genome, or may, in some instances, integrate into the genome itself In the present specification, "plasmid" and "vector" are sometimes used interchangeably as the plasmid is the most commonly used form of vector at present. However, the invention is intended to include such other forms of expression vectors which serve equivalent functions and which are, or become, known in the art, including but not limited to plasmids, phage particles, or simply potential genomic inserts.

The "host cells" used in the present invention generally are prokaryotic or eukaryotic hosts which contain an expression vector and/or gene of interest. Host cells are transformed or transfected with vectors constructed using recombinant DNA techniques. Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site (Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal.

The terms "stable transfection" and "stably transfected" refer to the introduction and integration of foreign DNA into the genome of the transfected cell. The term "stable transfectant" refers to a cell which has stably integrated foreign DNA into the genomic DNA.

The terms "selectable marker" and "selectable gene product" as used herein refer to the use of a gene which encodes an enzymatic activity that confers resistance to an antibiotic or drug upon the cell in which the selectable marker is expressed.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both. Gene amplification occurs naturally during development in particular genes such as the amplification of ribosomal genes in amphibian oocytes. Gene amplification may be induced by treating cultured cells with drugs. An example of drug-induced amplification is the methotrexate-induced amplification of the endogenous dhfr gene in mammalian cells (Schmike et al., Science 202:1051 [1978]). Selection of cells by growth in the presence of a drug (e.g., an inhibitor of an inhibitable enzyme) may result in the amplification of either the endogenous gene encoding the gene product required for growth in the presence of the drug or by amplification of exogenous (i.e., input) sequences encoding this gene product, or both.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the terms "restriction endonucleases" and "restriction enzymes" refer to bacterial enzymes, each of which cut double-stranded DNA at or near a specific nucleotide sequence.

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

In some embodiments, the present invention provides methods for the identification of CD4$^+$ T-cell epitopes in BMP sequences and the production of peptides that are capable of initiating the CD4$^+$ T-cell response. In particular, the present invention provides means and compositions suitable for altering the immunogenicity of BMP for use in various settings.

In these embodiments, the present invention provides means for determining the T-cell responses of humans against various epitopes comprising a protein of interest (e.g., BMP-7). In additional embodiments, once the significant epitopes are identified using the I-MUNE® assay system described herein, the significant epitopes are altered to produce epitopes that induce an altered immune response.

Thus, as indicated above, in some embodiments, the identification of immunogenic epitopes provides information needed to produce BMPs that exhibit modified immunogenic responses (e.g., antigenicity and/or immunogenicity) when compared to the native proteins encoded by their precursor DNAs.

DETAILED DESCRIPTION OF THE INVENTION

The present invention provides CD4+ T-cell epitopes in bone morphogenetic proteins (BMPs). In particular embodiments, the present invention provides CD4+ T-cell epitopes of BMP-7 and BMP-14. In some preferred embodiments, the present invention provides CD4+ T-cell epitopes of BMP-7 and BMP-14 that are suitable for modification to reduce the immunogenicity of (e.g., native) BMP-7 and BMP-14 proteins.

In preferred embodiments, the methods provided by the present invention involve the use of dendritic cells as antigen-presenting cells, 15-mer peptides offset by 3 amino acids that encompass an entire protein sequence of interest, and CD4$^+$ T-cells obtained from the dendritic cell donors. T-cells are allowed to proliferate in a sample in the presence of the peptides (each peptide is tested individually) and differentiated dendritic cells. It is not intended that any of the methods of the present invention be conducted in any particular order, as far as preparation of the PEPSETS™ and differentiation of dendritic cells. For example, in some embodiments, the PEPSETS™ are prepared before the dendritic cells are differentiated, while in other embodiments, the dendritic cells are differentiated before the PEPSETS™ are prepared, and in still other embodiments, the dendritic cells are differentiated and the PEPSETS™ are prepared concurrently. Thus, it is not intended that the present invention be limited to methods having these steps in any particular order.

If the proliferation in response to a peptide results in a stimulation index (SI) of 1.5 to at least 4.5, the response is considered and tallied as being "positive." The results for each peptide are tabulated for a donor set, which preferably reflects the general HLA allele frequencies of the population, albeit with some variation. The "structure value," based on the determination of difference from linearity is determined, and this value is used to rank the relative immunogenicity of the proteins. Thus, the present invention provides information useful in the modification of proteins, such that reduced response rates predicted to be effective in humans are achieved without the need to sensitize volunteers. Analyses of donor responses to peptide sets based on these new proteins that have been designed to be hypoimmunogenic are then conducted to calculate structure values for the new protein(s) and confirm their immunogenicity and exposure potentials.

The present invention also provides methods for determining the immune response of a test population against a test protein, comprising the steps of: (a) preparing a PEPSETS™ from a test protein; (b) obtaining a plurality of solutions comprising human dendritic cells and a plurality of solutions of naïve human CD4+ and/or CD8+ T-cells, wherein the solutions of human dendritic cells and solutions of naïve human CD4+ and/or CD8+ T-cells are obtained from a plurality of individuals within the test population; (c) differentiating the dendritic cells to produce a plurality of solutions comprising differentiated dendritic cells; (d) combining the plurality of the solutions of differentiated dendritic cells and the solutions of naïve CD4+ and/or CD8+ T-cells with the PEPSETS™, wherein each of the solutions of differentiated dendritic cells and the solutions of naïve CD4+ and/or CD8+ T-cells are from one individual within the test population are combined; (e) measuring proliferation of the T-cells in step (d), to determine the responses to each peptide in the PEPSETS™; (g) compiling the responses of the T-cells in step (e) for the test protein; (h) determining the structure value of the compiled responses of step (g) for the test protein; and (i) determining the level of exposure of the plurality of individuals to the test protein. In some preferred embodiments, the PEPSETS™ comprise peptides of about 15 amino acids in length, while in some particularly preferred embodiments each peptide overlaps adjacent peptides by about 3 amino acids. However, it is not intended that the peptides within the PEPSETS™ be limited to any particular length nor overlap, as other peptide lengths and overlap amounts find use in various embodiments of the present invention. In some embodiments, at least two test proteins are tested. In some preferred embodiments, the level of exposure of the plurality of individuals to the test protein is compared. In some particularly preferred embodiments, the test protein is modified to produce a variant protein that exhibits a reduced immunogenic response in the test population. The present invention also provides means to categorize proteins based on both their background percent response and their structure values. Thus, in some further embodiments, the proteins analyzed are categorized and/or ranked according to their background percent response and structure values.

In some preferred embodiments, the invention provides an assay system (i.e., the I-MUNE® assay) for ranking relative immunogenicity of proteins. In one embodiment, the methods comprise measuring in vitro $CD4^+$ T-cell proliferation in response to peptide fragments of a protein, compiling the measured responses for the protein, determining the structure value of the compiled responses, and comparing the structure value of the protein to the structure value of a second protein, wherein the protein comprising the lowest structure value is ranked as being less immunogenic to a human compared to a protein having a higher structure value. In a further embodiment, the T-cell proliferation of each peptide fragment and each protein is determined in side-by-side tests. In other embodiments, a "positive" response is determined based on an SI value between 2.7 and 3.2. In particularly preferred embodiments, the level of proliferation results in a stimulation index of 2.95 or greater.

The present invention also provides methods for assessing the reduced immunogenic capacity of variant proteins such as BMP-7 and BMP-14 in humans. In some embodiments, the methods comprise reducing one or more prominent regions of a parent protein to a background level to create a variant protein, determining the structure value of the variant, and comparing the structure value of the variant with the structure value of the parent protein, wherein the lower structure value indicates a protein with reduced immunogenicity. In further embodiments, the number of prominent regions reduced to background level are between 1 and 10, preferably between 1 and 5. In yet another embodiment, one or more amino acid residues are altered in the prominent region of the parent protein to create a variant. The present invention also provides methods for selecting the least immunogenic protein from a group of related proteins.

It is contemplated that reduction in the immunogenicity of these proteins, particularly BMP-7, will find use in various treatment regimes. For example, BMP-7 has been used to assist in correcting spinal problems in certain patients for quite some time (See e.g., Walker and Wright, Neurosurg. Focus 13(6):1-13 [2002]; and Poynton and Lane, Spine 27:540-548 [2002]). This is of significance as 38% of these treated patients developed detectable anti-BMP antibodies. Thus, these patients now produce antibodies against a naturally occurring endogenous human protein. In addition, during the development of the present invention, it was observed that peripheral mononuclear cells from normal community donors make high levels of IL-2, IFN-gamma, and IL-4, in response to BMP-7 epitope peptides in a 3-hour co-culture assay system. Thus, it appears that not only is the BMP-7 protein immunogenic, random individuals also carry memory CD4+ T cell responses to the BMP-7 epitope peptides. It is contemplated that modifying the BMP-7 protein to reduce the immunogenicity will find use as a substitute treatment means that will avoid the potential dangers of anti-BMP-7 antibodies.

The present invention further provides methods of using the relative ranking of related proteins to determine T-cell epitope modification suitable to reduce the immunogenicity of the proteins, particularly in humans. The present invention also provides means to categorize proteins based on both their background percent response and their structure values. Thus, in some further embodiments, the proteins analyzed are categorized and/or ranked according to their background percent response and structure values.

In some embodiments, the present invention provides methods for ranking the relative immunogenicity of a first protein and at least one additional protein, comprising the steps of: (a) preparing a first PEPSETS™ from a first protein and preparing at least one additional PEPSET™ from each of the additional proteins, wherein each of the PEPSETS™ (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first PEPSETS™; (e) combining the solution of differentiated dendritic cells and the naïve CD4+ and/or CD8+ T-cells with each of the PEPSETS™ from the additional proteins; measuring proliferation of the T-cells in steps (d) and (e), to determine the responses to each peptide in the first and additional PEPSETS™; (g) compiling the responses of the T-cells in step (f) for the first protein and the additional proteins; (h) determining the structure value of the compiled responses of step (g) for the first protein and the additional proteins; and (i) comparing the structure value obtained for the first protein with the structure value for the additional proteins to determine the immunogenicity ranking of the first protein and the additional proteins. In some preferred embodiments, the PEPSETS™ comprise peptides of about 15 amino acids in length, while in some particularly preferred embodiments each peptide overlaps adjacent peptides by about 3 amino acids. However, it is not intended that the peptides within the PEPSETS™ be limited to any particular length nor overlap, as other peptide lengths and overlap amounts find use in various embodiments of the present invention.

In some embodiments, the protein having the lowest structure value is ranked as being less immunogenic than the protein having the higher structure value. In further embodiments, a positive response against the first protein comprises a stimulation index value between about 2.7 and about 3.2. In yet other embodiments, a positive response against the additional proteins comprises a stimulation index value between about 2.7 and about 3.2. In further embodiments, a positive response against the first protein comprises a stimulation index value between about 2.7 and about 3.2 and a positive response against the additional proteins comprises a stimulation index value between about 2.7 and about 3.2. In some embodiments, proliferation of the T-cells in steps (d) results in a stimulation index of about 2.95 or greater, while in additional embodiments, the proliferation of the T-cells in steps (e) results in a stimulation index of about 2.95 or greater. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. The present invention also provides means to categorize proteins based on both their background percent response and their structure values. Thus, in some further embodiments, the proteins analyzed are categorized and/or ranked according to their background percent response and structure values.

The present invention also provides methods for ranking the relative immunogenicity of two proteins, wherein the second protein is a protein variant of the first protein, comprising the steps of: (a) preparing a first PEPSETS™ from a first protein and a second PEPSETS™ from a second protein; (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first PEPSETS™; (e) combining the solution of differentiated dendritic cells and the naïve CD4+ and/or CD8+ T-cells with the second PEPSETS™; (f) measuring proliferation of the T-cells in steps (d) and (e), to determine the responses to each peptide in the first and second PEPSETS™; (g) compiling the responses of the T-cells in step (f) for the first protein and the second protein; (h) determining the structure value of the compiled responses of step (g) for the first protein and the second protein; (i) comparing the structure value obtained for the first protein with the structure value for the second protein to determine the immunogenicity ranking of the first protein and the second protein. In some embodiments, the second protein is ranked as less immunogenic than the first protein, while in alternative embodiments, the first protein is ranked as less immunogenic than the second protein. In some preferred embodiments, the PEPSETS™ comprise peptides of about 15 amino acids in length, while in some particularly preferred embodiments each peptide overlaps adjacent peptides by about 3 amino acids. However, it is not intended that the peptides within the PEPSETS™ be limited to any particular length nor overlap, as other peptide lengths and overlap amounts find use in various embodiments of the present invention. In still further embodiments, a positive response against the first protein comprises a stimulation index value between about 2.7 and about 3.2, while in other embodiments, a positive response against the second protein comprises a stimulation index value between about 2.7 and about 3.2. In additional embodiments, a positive response against the first protein comprises a stimulation index value between about 2.7 and about 3.2 and a positive response against the second protein comprises a stimulation index value between about 2.7 and about 3.2. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. In some embodiments, the second protein comprises a reduction of at least one prominent region in the first protein. In further embodiments, the proliferation of the T-cells in step (e) is at a background level. In some particularly preferred embodiments, the structure values obtained for each of the human blood sources and the proteins are compared. The present invention also provides means to categorize proteins based on both their background percent response and their structure values. Thus, in some further embodiments, the proteins analyzed are categorized and/or ranked according to their background percent response and structure values.

The present invention also provides methods for ranking the relative immunogenicity of a first protein and at least one variant protein, comprising the steps of: (a) preparing a first PEPSET™ from a first protein and PEPSETS™ from each of the variant proteins; (b) obtaining from a single human blood source a solution comprising dendritic cells and a solution of naïve CD4+ and/or CD8+ T-cells; (c) differentiating the dendritic cells to produce a solution of differentiated dendritic cells; (d) combining the solution of differentiated dendritic cells and the naïve CD4+ and/or CD8+ T-cells with the first pepset; (e) combining the solution of differentiated dendritic cells and the naïve CD4+ and/or CD8+ T-cells with each pepset prepared from each of the variant proteins; (f) measuring proliferation of the T-cells in steps (d) and (e), to determine the responses to each peptide in the first and second PEPSETS™; (g) compiling the responses of the T-cells in step (f) for the first protein and the variant protein(s); (h) determining the structure value of the compiled responses of step (g) for the first protein and the variant protein(s); and (i) comparing the structure value obtained for the first protein with the structure value for the variant protein(s) to determine the immunogenicity ranking of the first protein and the variant proteins. In some preferred embodiments, the PEPSETS™ comprise peptides of about 15 amino acids in length, while in some particularly preferred embodiments each peptide overlaps adjacent peptides by about 3 amino acids. However, it is not intended that the peptides within the PEPSETS™ be limited to any particular length nor overlap, as other peptide lengths and overlap amounts find use in the present invention. In some preferred embodiments, at least one of the variant proteins is ranked as less immunogenic than the first protein, while in other embodiments, the first protein is ranked as less immunogenic than at least one of the variant proteins. In further embodiments, a positive response against the first protein comprises a stimulation index value between about 2.7 and about 3.2, while in other embodiments, a positive response against a variant protein comprises a stimulation index value between about 2.7 and about 3.2. In additional embodiments, a positive response against the first protein comprises a stimulation index value between about 2.7 and about 3.2 and a positive response against a variant protein comprises a stimulation index value between about 2.7 and about 3.2. In still further embodiments, the proliferation of the T-cells in steps (d) results in a stimulation index of about 2.95 or greater and the proliferation of the T-cells in steps (e) results in a stimulation index of about 2.95 or greater. In some particularly preferred embodiments, at least one additional human blood source is used in step (b). In some additional particularly preferred embodiments, the structure values obtained for each of the human blood sources and the proteins are compared. In some embodiments, the variant protein comprises a reduction of at least one prominent region in the first protein. In further embodiments, the proliferation of the T-cells in step (e) is at a background level. In some preferred embodiments, the proliferation of the T-cells in step (e) for at least one variant protein is at a background level. In some particularly preferred embodiments, the structure values obtained for each of the human blood sources and the proteins are compared. In further embodiments, at least one additional human blood source is used in step (b). The present invention also provides means to categorize proteins based on both their background percent response and their structure values. Thus, in some further embodiments, the proteins analyzed are categorized and/or ranked according to their background percent response and structure values.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); PBS (phosphate buffered saline); g (gravity); RR (relative risk); OD (optical density); Dulbecco's phosphate buffered solution (DPBS); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); DMSO (dimethyl sulfoxide); EGTA (ethylene glycol-bis(β-aminoethyl ether) N,N,N',N'-tetraacetic acid); EDTA (ethylenediaminetetracetic acid); DPBS (Dulbecco's phosphate buffered solution); bla (β-lactamase or ampicillin-resistance gene); Endogen (Endogen, Woburn, Mass.); CytoVax (CytoVax, Edmonton, Canada); Wyeth-Ayerst (Wyeth-Ayerst, Philadelphia, Pa.); NEN (NEN Life Science Products, Boston, Mass.); Wallace Oy (Wallace Oy, Turku, Finland); Pharma AS (Pharma AS, Oslo, Norway); Dynal (Dynal, Oslo, Norway); Bio-Synthesis (Bio-Synthesis, Lewisville, Tex.); Mimotopes (Mimotopes, Inc., San Diego, Calif.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Piscataway, N.J.); Invitrogen (Invitrogen, Inc., Grand Island, N.Y.); Abbott (Abbott Laboratories, Abbott Park, Ill.); List (List Biological Laboratories Inc., Campbell, Calif.); Perkin Elmer (PerkinElmer Life Sciences, Boston Mass.); and Stratagene (Stratagene, La Jolla, Calif.).

Example 1

Preparation of BMP Epitopes

Full length amino acid sequences of human BMP-7 (GenBank Accession No. P18075) and BMP-14 (GenBank Accession No. P43026) precursor proteins were used to create 15-mer peptide sets. These variant peptides were synthesized by Mimotopes, using the multi-pin synthesis technique known in the art (See e.g., Maeji et al., J. Immunol. Meth., 134:23-33 [1990]). The 15-mer peptides were created such that sequences with adjacent peptides shared 12 amino acids (i.e., each peptide was offset by three amino acids). Peptides were diluted with DMSO to provide a stock concentration of approximately 2 mg/ml. The final concentration of peptides used in each assay was 5 μg/ml.

Example 2

Preparation of Cells Used in the Assay System for the Identification of Peptide T-Cell Epitopes in BMP-7 and BMP-14

Fresh human peripheral blood cells were collected from 83 community donors. These cells were tested to determine antigenic epitopes in BMP-7 and BMP-14, as described in Example 3, below.

Peripheral mononuclear blood cells (PBMCs) (stored at room temperature, no older than 24 hours) were prepared for use as follows. PBMCs were isolated from buffy coat material by centrifuging over an underlay of LYMPHOPREP™ at 1000×g for 30 minutes. The interface layer was collected and washed and counted using the CELL-DYN® 3700 System (Abbott). Then, suspensions containing $10^8$ PBMCs resuspended in 30 ml of AIM-V (Invitrogen) were prepared and the cells were allowed to adhere to plastic T-75 culture flasks for two hours. The remainder of the cells were frozen at $5\times10^7$ cells/ml in 90% FCS (Gibco/BRL) and 10% DMSO (Sigma).

After the two hour PBMC incubation period, non-adherent cells were removed from the culture flasks. The adherent cells were cultured in the flasks with 800 units/ml recombinant human GM-CSF (Endogen) and 100 units/ml recombinant human IL4 (Endogen) at 37° C., 5% $CO_2$. On day 5 of incubation, 50 units/ml recombinant human Il-1α (Endogen) and 0.2 units/ml recombinant human TNF-α were added to the cultures. Adherent and non-adherent dendritic cells were harvested, washed, and counted on day 7, following a one-hour treatment with 30 mg/ml mitomycin C (Sigma) and 10 mM EDTA.

Autologous CD4+ T-cells were prepared from frozen aliquots of PBMCs. After thawing and washing in DPBS, CD4+ T-cells were isolated using a commercially available CD4 negative selection kit (Dynal), according to the manufacturer's instructions. Cells were counted using the Abbott CELL-DYN® 3700 System. The purity obtained using these methods was generally found to be greater than 90%.

Example 3

T-Cell Proliferation Assays

This Example describes the assay system used in the present invention. This test system is also referred to as the "I-MUNE®" assay system. In 96-well, round bottom plates, autologous dendritic cells and CD4+ T-cells were combined with test peptides. More specifically, in a volume of 100 μl/well, $2\times10^4$ dendritic cells in AIM V were combined with individual peptides (at a final peptide concentration of 5 μg/ml and a final DMSO concentration of 0.25%). After a one-hour incubation at 37° C., 5% $CO_2$, $2\times10^5$ CD4+ T-cells were added to the culture for a total volume of 200 μl. Negative control wells contained dendritic cells, CD4+ T-cells and 0.25% DMSO. Positive control wells contained dendritic cells, CD4+ T-cells (at the same concentrations as the test wells) and 0.25% DMSO with 0.4 μg/ml tetanus toxoid (List). Individual peptides were tested in duplicate for each donor.

After 5 days of incubation at 37° C., 5% $CO_2$, the cultures were pulsed with 0.25 μCi/well tritiated thymidine (Perkin Elmer). After a subsequent 24 hours of incubation, plates were harvested and assessed for incorporation of the tritiated thymidine (i.e., T-cell proliferation) using a Wallac MICROBETA® TriLux liquid scintillation counter (Perkin Elmer).

Example 4

Data Analyses

For each individual buffy coat sample, the average CPM values for all of the peptides were analyzed. The average CPM values for each peptide were divided by the average CPM value for the control (DMSO only) wells to determine the "stimulation index" (SI). Donors were tested with each peptide set until an average of at least two responses per peptide were compiled. The data for each protein were graphed showing the percent responders to each peptide within the set. A positive response was collated if the SI value was equal to or greater than 2.95. This value was chosen because it approximates a difference of three standard deviations in a normal population distribution. For each protein assessed, positive responses to individual peptides by individual donors were compiled.

To determine the background response for a given protein, the percent responders for each peptide in the set were averaged and a standard deviation was calculated. SI values for each donor were compiled for each peptide set, and the percent of responders reported. The average background response rate for each peptide set was calculated by averaging the percent response for all of the peptides in the set. The statistical significance was calculated as described below, using Poisson statistics for the number of responders to each peptide within the dataset. These statistical methods are used in addition to the "major" and "minor" determinant designations. As described herein, some of the BMP-7 epitopes are "major" because they meet the 3 standard deviation definition. The statistical significance of the peptide responses were calculated based on Poisson statistics. The average frequency of responders was used to calculate a Poisson distribution based on the total number of responses and the number of peptides in the set. A response was considered significant if $p<0.05$. In addition, two-tailed Student's t-tests with unequal variance, were performed. For epitope determination using data with low background response rates, a conservative Poisson based formula was applied:

$$= 1 - e\left(-n\left(1 - \sum \frac{\lambda^x e^{-\lambda}}{x!}\right)\right)$$

where n=the number of peptides in the set, x=the frequency of responses at the peptide of interest, and λ=the median frequency of responses within the dataset. For epitope determinations based on data with a high background response rate, the less stringent Poisson based determination $$1 - \left(\sum_{i=0}^{x} \frac{\lambda^x e^{-\lambda}}{x!}\right)$$

was used, where λ=the median frequency of responses in the dataset, and x=the frequency of responses at the peptide of interest.

In some data analyses, the data were examined for inconsistencies in the experimental duplicates and non-duplicating values were discarded. Data were also discarded from the dataset if the tetanus positive control did not induce proliferation. The results of this analysis are shown in FIG. 1 (indicated as "QC" method). The structure values obtained for these two proteins analyzed by this method indicate that BMP-7 is more immunogenic than BMP-14. BMP-7 is remarkable for the number and robustness of the epitope responses observed, especially considering that this is a human protein. The epitope sequences of interest are shown in Tables 1 and 2, below. In the BMP-7 peptide set, the values for peptide 41 did not reach the $p<0.05$ cut-off, but were the next largest values in the dataset (i.e., these are "minor" epitopes). In the BMP-14 dataset, the values for peptides 19 and 20 did not reach the $p<0.05$ cut-off, but were the next largest values in the dataset (i.e., "minor" epitopes).

TABLE 1

| BMP-7 Peptides | | |
|---|---|---|
| Peptide Number | Amino Acid Sequence | SEQ ID NO: |
| 3 | RSQNRSKTPKNQEAL | (SEQ ID NO: 1) |
| 7 | EALRMANVAENSSSD | (SEQ ID NO: 2) |
| 8 | RMANVAENSSSDQRQ | (SEQ ID NO: 3) |
| 16 | SFRDLGWQDWIIAPE | (SEQ ID NO: 4) |
| 41 | SNVILKKYRNMVVRA | (SEQ ID NO: 5) |

TABLE 2

| BMP-14 Peptides | | |
|---|---|---|
| Peptide Number | Amino Acid Sequence | SEQ ID NO: |
| 31 | SPISILFIDSANNVV | (SEQ ID NO: 6) |
| 19 | PLRSHLEPTNHAVIQ | (SEQ ID NO: 7) |
| 20 | SHLEPTNHAVIQTLM | (SEQ ID NO: 8) |

Figure 2:
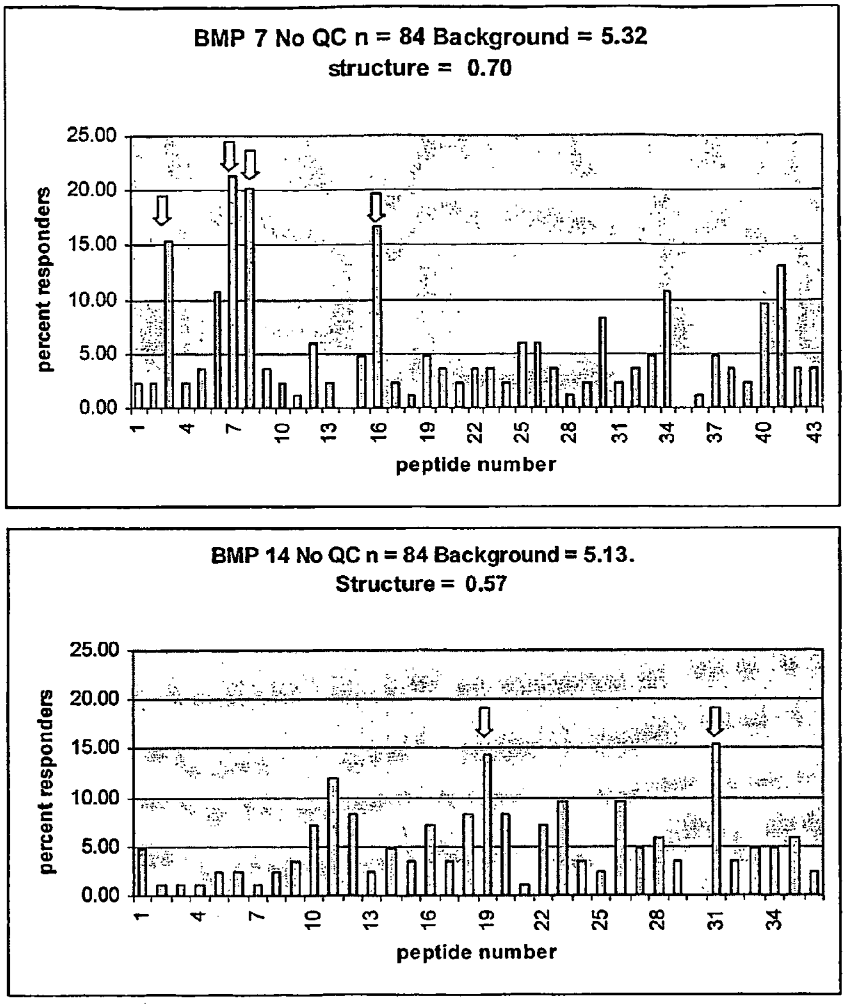
FIG. 2 provides two graphs that illustrate the percent of responders from a population of 83 random individuals tested with peptides derived from BMP-7 (Panel A) and BMP-14 (Panel B). The background and structure values are also indicated. The consecutive 15-mer peptides offset by 3 amino acids are listed on the x-axis (indicated by the "peptide number") and the percentages of donors who responded to each peptide are shown on the y-axis.

In other analyses, no data were eliminated, regardless of whether or not they duplicated (the "non-QC" method). This analysis method resulted in a higher overall background response for proteins tested in this less rigorous manner. However, the CD4+ T-cell epitopes determined by Poisson distribution analysis (cut off $p<0.05$) within the peptide dataset identified a largely similar set of epitopes. These results are shown in FIG. 2 (indicated as "No QC"). Consistent with the results of the more rigorous analysis method described above, the BMP-7 protein was found to be more immunogenic than the BMP-14 protein. As noted, the epitope responses are still striking in BMP-7.

The structure values for BMP-7 and BMP14 were 0.70 and 0.57. The lower structure value for BMP-14 provides strong evidence for the comparative hypoimmunogenicity of BMP-14 as compared to BMP-7. This would suggest that if an application could use either BMP-7 or BMP-14, BMP-14 would be the preferred composition. However, it is not intended that the present invention be limited to the use of BMP-14 or BMP-7 epitopes, as it is contemplated that both will find use in different settings.

Example 5

Stimulation Index

Figure 3:
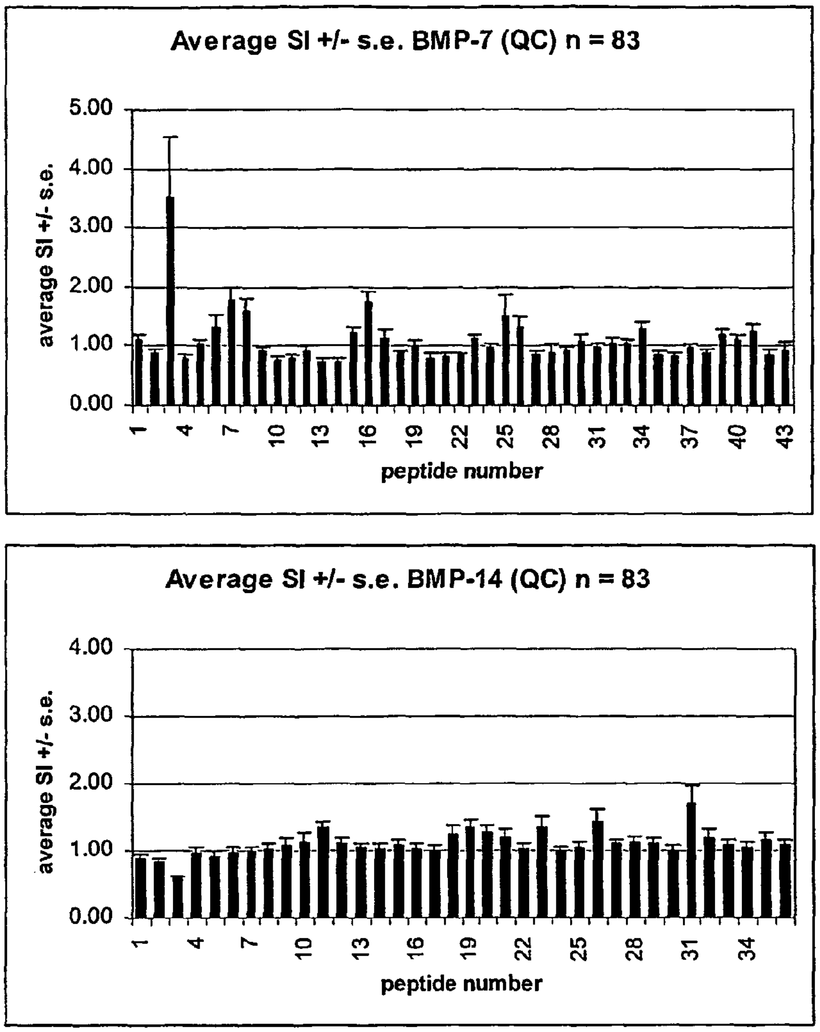
FIG. 3 provides two graphs that illustrate the average stimulation index (SI) of responses from a population of 83 random individuals tested with peptides derived from BMP-7 (Panel A) and BMP-14 (Panel B). The dataset was analyzed using the QC method. The average SI is shown for each peptide +/− standard error of the mean. The consecutive 15-mer peptides offset by 3 amino acids are listed on the x-axis (indicated by the "peptide number") and the average SI is shown on the y-axis.
Figure 4:
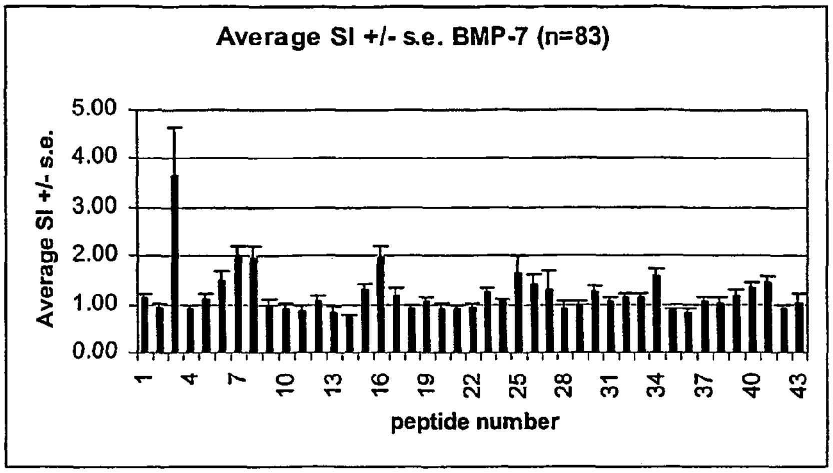
FIG. 4 provides two graphs that illustrate the average stimulation index (SI) of responses from a population of 83 random individuals tested with peptides derived from BMP-7 (Panel A) and BMP-14 (Panel B). The dataset was analyzed using the non-QC method. The average SI is shown for each peptide +/− standard error of the mean. The consecutive 15-mer peptides offset by 3 amino acids are listed on the x-axis (indicated by the "peptide number") and the average SI is shown on the y-axis.
Figure 4:
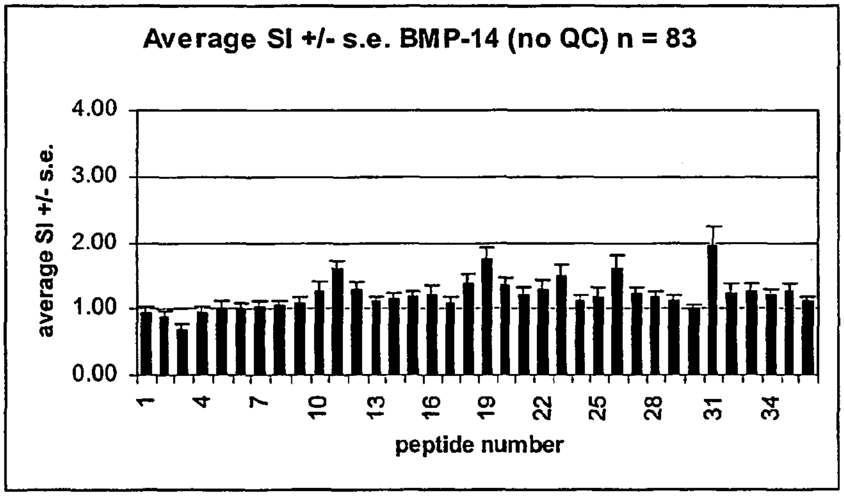

In addition to the above analyses, the average stimulation indices or both BMP-7 and BMP-14 were determined. The stimulation index values for all 83 donors were averaged. The results are shown for QC data in FIG. 3 and non-QC data in FIG. 4. The peptide responses detailed above are supported by more robust proliferative responses over all the donors. The magnitude of the proliferative responses to peptide epitopes in the BMP-7 peptide set were found to be higher than the responses in the BMP-14 peptide set. Since these peptide sets were tested parametrically in 83 donors, this result supports the structure value determination that BMP-7 is more immunogenic overall than BMP-14.

Example 6

HLA Associations

In addition to the above analyses, the HLA associations with BMP-7 and BMP-14 epitope peptides were determined. In these experiments, the proliferative response data to five epitope peptides (#3, #7, #8, #16 and #31) were tested in 83 donors for which the expression of HLA Class II antigens at DRB1 and DQB1 was also tested. For four of the peptides, the reaction was assessed by two methods (i.e., "QC" and "non-QC," "[nQC"] as described above). The statistically significant associations found by both methods were as follows. For epitope #3 and DR11, the relative risk (RR) was 6.25; $p<0.0005$ [QC], RR=4.17 $p<0.005$ [nQC]. For epitope #3 and DQ2, the RR was 0.17 $p<0.04$ [QC], RR=0.13 $p<0.01$ [nQC]. For epitope #3 and DQ9, the RR was 6.67 $p<0.003$ [QC]; RR=4.85 $p<0.013$ [nQC]. For epitope #8 and DR11, the RR was 6.6 $p<0.0003$. For epitope #31 and DR7, the RR was 8.32 $p<0.001$ [QC]; RR=4.44 $p<0.002$ [nQC].

In addition the average stimulation index (SI) was higher among DR11+ than among DR11− donors for peptide #3 (QC) (5.8 fold, $p<0.0004$) and peptide #8 (2.3 fold $p<0.007$). Also the average SI was higher among DR7+ than among DR7− donors for peptide #31 (QC) (2.7 fold $p<0.0007$).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, immunology, and/or related fields are intended to be within the scope of the present invention.

I claim:

1. A method of reducing the immunogenicity of a protein, wherein said protein is selected from the group consisting of BMP-7 and BMP 14, comprising:

modifying said protein to neutralize a T-cell epitope to produce a variant protein, such that said variant protein induces less than or substantially equal to the baseline proliferation of naïve T-cells;

wherein the amino acid sequence of said T-cell epitope is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

2. The method of claim 1, wherein said T-cell epitope is modified by substituting a portion of the amino acid sequence of said T-cell epitope with an analogous sequence from a homolog of said protein.

3. The method of claim 1, wherein said T-cell epitope is modified by substituting the amino acid sequence of said T-cell epitope with a sequence which substantially mimics the major tertiary structure attributes of said T-cell epitope.

4. A method for producing a variant protein having reduced allergenicity comprising:

modifying at least one amino acid in a T-cell epitope region of a naturally-occurring protein to produce said variant protein; wherein said naturally-occurring protein is selected from the group consisting of BMP-7 and BMP-14; and wherein the amino acid sequence of said T-cell epitope region is selected from the group consisting of SEQ ID NO:1, SEQ ID NO:2, SEQ ID NO:3, SEQ ID NO:4, SEQ ID NO:5, SEQ ID NO:6, SEQ ID NO:7 and SEQ ID NO:8.

5. The method of claim 4, further comprising the step of comparing the ability of said T-cell epitope region of said naturally-occurring protein to stimulate proliferation of said naïve human CD4+ or CD8+ T-cells with the ability of a modified T-cell epitope region of said variant protein to stimulate proliferation of said naïve human CD4+ or CD8+ T-cells.

* * * * *

SEQUENCE LISTING

```
<160> NUMBER OF SEQ ID NOS: 8

<210> SEQ ID NO 1
<211> LENGTH: 15
<212> TYPE: PRT
<213> ORGANISM: Artificial Sequence
<220> FEATURE:
<223> OTHER INFORMATION: BMP-7 epitope

<400> SEQUENCE: 1

Arg Ser Gln Asn Arg Ser Lys Thr Pro Lys Asn Gln Glu Ala Leu
 1               5                  10                  15


<210> SEQ ID NO 2
<211> LENGTH: 15
<212> TYPE: PRT
<213> ORGANISM: Artificial Sequence
<220> FEATURE:
<223> OTHER INFORMATION: BMP-7 epitope

<400> SEQUENCE: 2

Glu Ala Leu Arg Met Ala Asn Val Ala Glu Asn Ser Ser Ser Asp
 1               5                  10                  15


<210> SEQ ID NO 3
<211> LENGTH: 15
<212> TYPE: PRT
<213> ORGANISM: Artificial Sequence
<220> FEATURE:
<223> OTHER INFORMATION: BMP-7 epitope
```

-continued

```
<400> SEQUENCE: 3

Arg Met Ala Asn Val Ala Glu Asn Ser Ser Ser Asp Gln Arg Gln
 1               5                   10                  15


<210> SEQ ID NO 4
<211> LENGTH: 15
<212> TYPE: PRT
<213> ORGANISM: Artificial Sequence
<220> FEATURE:
<223> OTHER INFORMATION: BMP-7 epitope

<400> SEQUENCE: 4

Ser Phe Arg Asp Leu Gly Trp Gln Asp Trp Ile Ile Ala Pro Glu
 1               5                   10                  15


<210> SEQ ID NO 5
<211> LENGTH: 15
<212> TYPE: PRT
<213> ORGANISM: Artificial Sequence
<220> FEATURE:
<223> OTHER INFORMATION: BMP-7 epitope

<400> SEQUENCE: 5

Ser Asn Val Ile Leu Lys Lys Tyr Arg Asn Met Val Val Arg Ala
 1               5                   10                  15


<210> SEQ ID NO 6
<211> LENGTH: 15
<212> TYPE: PRT
<213> ORGANISM: Artificial Sequence
<220> FEATURE:
<223> OTHER INFORMATION: BMP-14 epitope

<400> SEQUENCE: 6

Ser Pro Ile Ser Ile Leu Phe Ile Asp Ser Ala Asn Asn Val Val
 1               5                   10                  15


<210> SEQ ID NO 7
<211> LENGTH: 15
<212> TYPE: PRT
<213> ORGANISM: Artificial Sequence
<220> FEATURE:
<223> OTHER INFORMATION: BMP-14 epitope

<400> SEQUENCE: 7

Pro Leu Arg Ser His Leu Glu Pro Thr Asn His Ala Val Ile Gln
 1               5                   10                  15


<210> SEQ ID NO 8
<211> LENGTH: 15
<212> TYPE: PRT
<213> ORGANISM: Artificial Sequence
<220> FEATURE:
<223> OTHER INFORMATION: BMP-14 epitope

<400> SEQUENCE: 8

Ser His Leu Glu Pro Thr Asn His Ala Val Ile Gln Thr Leu Met
 1               5                   10                  15
```